(12) United States Patent
Kiely et al.

(10) Patent No.: US 10,973,862 B2
(45) Date of Patent: Apr. 13, 2021

(54) BIFIDOBACTERIUM LONGUM FOR TREATING OBESITY AND ASSOCIATED METABOLIC DISORDERS

(71) Applicant: Alimentary Health Limited, Cork (IE)

(72) Inventors: Barry Kiely, Cork (IE); Eileen Frances Murphy, Cork (IE); Selena Healy, Tipperary (IE)

(73) Assignee: PrecisionBiotics Group Limited, Cork (IE)

( * ) Notice: Subject to any disclaimer, the term of this patent is extended or adjusted under 35 U.S.C. 154(b) by 131 days.

(21) Appl. No.: 16/060,765

(22) PCT Filed: Dec. 9, 2016

(86) PCT No.: PCT/EP2016/080454
§ 371 (c)(1),
(2) Date: Jun. 8, 2018

(87) PCT Pub. No.: WO2017/097987
PCT Pub. Date: Jun. 15, 2017

(65) Prior Publication Data
US 2019/0111090 A1    Apr. 18, 2019

(30) Foreign Application Priority Data
Dec. 11, 2015 (EP) .................................... 15199660

(51) Int. Cl.
| | | |
|---|---|---|
| *A61K 35/745* | (2015.01) | |
| *C12N 1/20* | (2006.01) | |
| *C12R 1/01* | (2006.01) | |
| *A23L 33/00* | (2016.01) | |
| *A23L 33/135* | (2016.01) | |
| *A61P 3/04* | (2006.01) | |

(52) U.S. Cl.
CPC .......... *A61K 35/745* (2013.01); *A23L 33/135* (2016.08); *A23L 33/30* (2016.08); *A61P 3/04* (2018.01); *C12N 1/20* (2013.01); *C12R 1/01* (2013.01); *A23V 2002/00* (2013.01); *A23V 2200/3204* (2013.01); *A23V 2200/332* (2013.01)

(58) Field of Classification Search
CPC ..... A61K 35/745; A23L 33/30; A23L 33/135; A61P 3/04
USPC ....................................................... 424/93.4
See application file for complete search history.

(56) References Cited

U.S. PATENT DOCUMENTS

2013/0261071 A1   10/2013   Grant et al.

FOREIGN PATENT DOCUMENTS

| RU | 2473681 C2 | 1/2013 |
| RU | 2570557 C2 | 12/2015 |
| WO | 2010055499 A2 | 5/2010 |
| WO | 2011058535 A1 | 5/2011 |

OTHER PUBLICATIONS

Stone, Major Health Benefits of Bifidobacterium Longum, Oct. 18, 2017, Available Online at: balanceone.com/blogs/news/bifidobacterium-longum.*

Di Gioia et al. "Bifidobacteria: their impact on gut microbiota composition and their applications as probiotics in infants," Applied Microbiology and Biotechnology, Springer, DE, vol. 98, No. 2, Nov. 2013, pp. 563-577.

Malaguarnera et al. "Bifidobacterium longum with Fructo-Oligosaccharides in Patients with Non Alcoholic Steatohepatitis," Digestive Diseases and Sciences, Kluwer Academic Publishers—Plenum Publishers, vol. 57, No. 2, Sep. 2011, pp. 545-553.

Pena et al. "Effect of the Synbiotic (*B. animalis* spp. *lactis* Bb12 + Oligofructose) in obese subjects. A randomized, double-blind, controlled clinical trial," Journal of Food and Nutrition Research, vol. 2, No. 8, Aug. 2014, pp. 491-498.

Shen et al. "The gut microbiota, obesity and insulin resistance," Molecular Aspects of Medicine, vol. 34, No. 1, Feb. 2013, pp. 39-58.

International Search Report dated Mar. 31, 2017, in International Application No. PCT/EP2016/080454 (6 pages).

Cruchet, S. et al., "The Use of Probiotics in Pediatric Gastroenterology: A Review of the Literature and Recommendations by Latin-American Experts," *Pediatric Drugs*, vol. 17, pp. 199-216 (Mar. 2015).

Dietrich, C.G. et al., "Commercially Available Probiotic Drinks Containing *Lactobacillus casei*, DN-114001 Reduce Antibiotic-Associated Diarrhea", World J. Gastroenterology, vol. 20, No. 42, pp. 15837-15844 (Nov. 2014).

Food and Agriculture Organization of the United Nations and World Health Organization, "Joint FAO/WHO Working Group Report on Drafting Guidelines for the Evaluation of Probiotics in Food", London Ontario, Canada (Apr. and May 2002) (11 pages).

López, P. et al, "Immune Response to *Bifidobacterium bifidum* Strains Support Treg/Th 17 Plasticity," *PLoS One*, vol. 6, No. 9, pp. 1-9, (Sep. 2011).

McFarland, L.V. t al., "Strain-Specificity and Disease-Specificity of Probiotic Efficacy: A Systemac Review and Meta-Analysis," *Frontiers in Medicine*, vol. 5, article 124, pp. 1-14 (May 2018).

Medina, M. et al., "Differential Immunomodulatory Properties of *Bifidobacterium logum* Strains: Relevance to Probiotic Selection and Clinical Applications," *Clinical and Experimental Immunology*, vol. 150, pp. 531-538 (2007).

(Continued)

Primary Examiner — Jennifer M. H. Tichy
(74) Attorney, Agent, or Firm — Bookoff McAndrews, PLLC

(57) ABSTRACT

*Bifidobacterium longum* AH1362 (NCIMB 41715) produces a polysaccharide and increases energy excretion. The strain is used in the prevention or treatment of obesity and obesity-related metabolic syndrome.

18 Claims, 13 Drawing Sheets

Specification includes a Sequence Listing.

(56) References Cited

OTHER PUBLICATIONS

Sanders, M.E. et al., "Shared Mechanisms Among Probiotic Taxa: Implications for General Probiotic Claims," *Current Opinion in Biotechnology*, vol. 49, pp. 207-216 (2018).

* cited by examiner

1) Unpaired student t-test (Lean versus DIO)
2) One-way ANOVA followed by Tukeys multiple comparison test (DIO versus all strains)

\*\*\* $p<0.001$. \*\* $p<0.01$, \* $p<0.05$.

1) Unpaired student t-test (Lean versus DIO)
2) One-way ANOVA followed by Tukeys multiple comparison test (DIO versus all strains)

* $p<0.001$.  $p<0.01$, * $p<0.05$.

1) Unpaired student t-test (Lean versus DIO)
2) One-way ANOVA followed by Tukeys multiple comparison test (DIO versus all strains)
* p<0.001.  p<0.01, * p<0.05

1) Unpaired student t-test (Lean versus DIO)
2) One-way ANOVA followed by Tukeys multiple comparison test (DIO versus all strains)
    * $p<0.001$,  $p<0.01$, * $p<0.05$.

1) Unpaired student t-test (Lean versus DIO)
2) One-way ANOVA followed by Tukeys multiple comparison test (DIO versus all strains)
   * p<0.001.  p<0.01, * p<0.05.

1) Unpaired student t-test (Lean versus DIO)
2) One-way ANOVA followed by Tukeys multiple comparison test (DIO versus all strains)
   * p<0.001,  p<0.01, * p<0.05.

1) Unpaired student t-test (Lean versus DIO)
2) One-way ANOVA followed by Tukeys multiple comparison test (DIO versus all strains)
    * $p<0.001$.  $p<0.01$, * $p<0.05$.

1) Unpaired student t-test (Lean versus DIO)
2) One-way ANOVA followed by Tukeys multiple comparison test (DIO versus all strains)
   * p<0.001.  p<0.01, * p<0.05.

SEQUENCE LISTING

<160> NUMBER OF SEQ ID NOS: 3

<210> SEQ ID NO 1
<211> LENGTH: 495
<212> TYPE: DNA
<213> ORGANISM: Bifidobacterium longum

<400> SEQUENCE: 1

```
tgctgggatc acctcctttc tacggagaat tcagtcggat gttcgtccga cggtgtgcgc      60
cccgcgcgtc gcatggtgcg atggcggcgg ggttgctggt gtggaagacg tcgttggctt     120
tgccctgccg gtcgtgcggt gggtgcgggg tggtatggat gcgcttttgg gctcccggat     180
cgccacccca ggcttttgc ctggcgcgat tcgatgcccg tcgtgcctgg gggccggccg     240
tgtgccggcg cgatggcgtg gcggtgcgtg gtggcttgag aactggatag tggacgcgag     300
caaaacaagg gtttttgaat ctttgttttg ctgttgattt cgaatcgaac tctattgttc     360
gtttcgatcg ttttgtgatc attttagtg tgatgatttg tcgtctggga atttgctaga     420
```

```
ggaatacttg cggccatgca cttcgtggtg tgtgttgctt gcaagggcgt atggtggagg      480
ccttcgacca ccaga                                                      495

<210> SEQ ID NO 2
<211> LENGTH: 18
<212> TYPE: DNA
<213> ORGANISM: Unknown
<220> FEATURE:
<223> OTHER INFORMATION: synthesised sequence

<400> SEQUENCE: 2
ctggtgccaa ggcatcca                                                   18

<210> SEQ ID NO 3
<211> LENGTH: 19
<212> TYPE: DNA
<213> ORGANISM: Unknown
<220> FEATURE:
<223> OTHER INFORMATION: synthesised sequence

<400> SEQUENCE: 3
gctggatcac ctcctttct                                                  19
```

BIFIDOBACTERIUM LONGUM FOR TREATING OBESITY AND ASSOCIATED METABOLIC DISORDERS

CROSS-REFERENCE TO RELATED APPLICATIONS

This application is the U.S. national phase entry under 35 U.S.C. § 371 of International Application No. PCT/EP2016/080454, filed on Dec. 9, 2016, which claims benefit to European Patent Application No. 15199660.0, filed on Dec. 11, 2015.

SEQUENCE LISTING

This application contains a sequence listing, submitted electronically in ASCII format under the file name 00175-0005-00000_SL.txt, which is incorporated by reference herein in its entirety. The ASCII copy of the sequence listing was created on Jun. 8, 2018, and is 1,474 bytes in size.

INTRODUCTION

The invention relates to a strain of *Bifidobacterium longum*.

Obesity is one of the most serious public health challenges of the 21st century. Globally, approximately 13% of adults are obese with a further 39% considered overweight (WHO, 2015). Obesity is a multifactorial disorder which is the result of a long-term imbalance between energy intake and expenditure and is influenced by genetic and environmental factors. Obesity is characterized by insulin resistance and a chronic low-grade inflammation (Gregor and Hotamisligil, 2011, Kahn et al., 2006). The intimate interplay between the immune system, metabolism, and gut microbiota may play an important role in controlling obesity and metabolic homeostasis. Obesity increases the risk of developing and exacerbating a cluster of chronic metabolic disorders such as type 2 diabetes (T2DM), non-alcoholic fatty liver disease (NAFLD), hypertension, atherosclerosis, dyslipidemia and cardiovascular disease (Guh et al., 2009) with the prevalence of metabolic comorbidities increasing in-line with increasing BMI (Gupta el al., 2015). Obesity also increases the risk of developing serious and potentially life-threatening diseases such as allergy & asthma, osteoarthritis, gallbladder disease and Non-alcoholic steatohepatitis (NASH), a condition in which fat builds up in the liver and major cause of cirrhosis of the liver.

Metabolic syndrome, an increasingly common condition, refers to the combination of obesity, hyperlipidemia (high triglycerides), hypertension (high blood pressure) and glucose intolerance (high blood sugar) and low HDL cholesterol. These risk factors assist in identifying subjects at high risk of developing type2 diabetes (T2D) and cardio-vascular disease.

Non-alcoholic fatty liver disease (NAFLD) is a very common disorder and refers to a group of conditions where there is accumulation of excess fat in the liver of people who drink little or no alcohol.

The more severe form of NAFLD is called non-alcoholic steatohepatitis (NASH). NASH causes the liver to swell and become damaged. NASH tends to develop in people who are overweight or obese, or have diabetes, high cholesterol or high triglycerides.

A large body of clinical and experimental data shows that increased flux of free fatty acids from increased visceral adipose tissue can lead to NAFLD related with insulin resistance. Thus, individuals with obesity, insulin resistance, and dyslipidemia are at the greatest risk of developing NAFLD.

Since the observation that germ-free mice were found to be leaner than their conventionally-raised counterparts (Backhed et al., 2004) the contribution of the gut microbiota to the development of obesity is increasingly being investigated (Backhed et al., 2007, Cani et al., 2008b, Ridaura et al., 2013, Vrieze et al., 2012). The contribution of the gut microbiota to obesity is multifactorial and involves issues such as enhanced energy harvest and fat storage (Turnbaugh et al., 2006) altered metabolic pathways (Kotzampassi et al., 2014, Turnbaugh et al., 2009) and bacterial translocation leading to chronic low-grade inflammation (Cani et al., 2007, Cani el al., 2008a). The manipulation of gut microbiota by probiotics is therefore a potential therapeutic tool to help ameliorate obesity and improve metabolic health. *Lactobacillus* strains are commonly used as probiotics and have a body of evidence that supports heath benefit effects in vivo in a strain specific manner (Aronsson et al., 2010, Lee et al., 2006, Naito et al., 2011).

The mechanism of action of these strains are not well characterised. One group of molecules that are of interest are bacterial exopolysaccharides (EPS). EPS's are high-molecular-weight polymers that are composed of sugar residues and are secreted by bacteria into the surrounding environment. Exopolysaccharide (EPS)-producing bacteria have been shown to have immunomodulatory effects (Fanning et al., 2012, Hidalgo-Cantabrana et al., 2014, Vinderola et al., 2006, Volman et al., 2008, Jones et al., 2014). Many lactic acid bacteria (LAB) have the ability to synthesize EPS. However, EPS are heterogeneous molecules and differ in composition, charge and molecular structure which may account for the strain-specific bioactivity observed (Adams et al., 2008, Bland et al., 2004, Hidalgo-Cantabrana et al., 2012, Kankainen et al., 2009).

The chronic low-grade inflammation associated with obesity and metabolic disorders (Gregor and Hotamisligil, 2011) is one risk factor that could be targeted for manipulation by administration of probiotics to favourably influence the development of obesity. We have previously shown that another lactic acid bacterium, *B. longum* NCIMB41003, has anti-inflammatory effects. This bacterium has a substantial EPS coat. The EPS material also has an anti-inflammatory effect as described in WO2010055499A.

STATEMENTS OF INVENTION

The invention provides the deposited strain NCIMB 41715. A strain of *Bifidobacterium long* AH1362 was deposited with the NCIMB under accession number 41715, on May 10, 2010 under the terms of the Budapest Treaty at the National Collections of Industrial and Marine Bacteria Limited (NCIMB) Ferguson Building, Craibstone Estate, Bucksburn, Aberdeen, AB21 9YA, Scotland, UK.

According to one aspect the invention provides a composition for use in the prevention or treatment of obesity and obesity-related Metabolic Syndrome comprising an effective amount of the strain. The strain produces a polysaccharide and increases energy excretion. The strain was isolated from a faecal sample from a placebo-fed healthy adult volunteer.

The isolated strain of the invention may be used for reducing body fat accumulation in a subject. The strain may be used for blocking weight gain or reducing weight. The strain may be used for the treatment, prevention, or alleviation of a condition resulting from excessive body fat accumulation.

The invention also provides a method for preventing or treating obesity, comprising administering a composition comprising a strain deposited with the NCIMB under accession number NCIMB 41715 to a subject in need of preventing or treating obesity.

The invention further provides a method for preventing or treating obesity-related metabolic syndrome, comprising administering a composition comprising a strain of deposited with the NCIMB under accession number NCIMB 41715 to a subject in need of preventing or treating obesity-related metabolic syndrome.

The invention also provides a method for preventing or treating Non-alcoholic fatty liver disease (NAFLD), comprising administering a composition comprising a strain of *Bifidobacterium longum* AH1362 deposited with the NCIMB under accession number NCIMB 41715 to a subject in need of preventing or treating Non-alcoholic fatty liver disease (NAFLD).

The strain may be in the form of viable cells. The strain may be in the form of non-viable cells. The general use of probiotic bacteria is in the form of viable cells. However, use can also be extended to non-viable cells such as killed cultures, mixtures of viable and non-viable cultures or compositions containing beneficial factors expressed by the probiotic bacteria. This could include thermally killed micro-organisms or micro-organisms killed by exposure to altered pH or subjection to pressure or gamma irradiation. With non-viable cells product preparation is simpler, cells may be incorporated easily into pharmaceuticals and storage requirements are much less limited than viable cells. *Lactobacillus casei* YIT 9018 offers an example of the effective use of heat killed cells as a method for the treatment and/or prevention of tumour growth as described in U.S. Pat. No. 4,347,240.

The invention also provides a formulation which comprises a strain as described herein. The formulation may further comprise a probiotic material. The formulation may further comprise a prebiotic material. The formulation may further comprise a carrier. The carrier may be an ingestible carrier may a pharmaceutically acceptable carrier such as a capsule, tablet or powder. The ingestible carrier may be a food product such as acidified milk, yoghurt, frozen yoghurt, milk powder, milk concentrate, cheese spreads, dressings or beverages. Some examples include a fermented food product such as a fermented milk product. The formulation may further comprise a protein and/or peptide, in particular proteins and/or peptides that are rich in glutamine/glutamate, a lipid, a carbohydrate, a vitamin, mineral and/or trace element. The *Bifidobacterium* strain may be present in an amount of more than $10^6$ cfu per gram of the formulation. The formulation may further comprise an adjuvant. The formulation may further comprise a bacterial component. The formulation may further comprise a drug entity. The formulation may further comprise a biological compound. In all cases the formulation comprises a strain as described herein and may include a carrier or other agent. Such a carrier or other agent in some cases do not occur in nature. The formulation may in some cases be used for immunisation and vaccination protocols.

The invention also provides a freeze-dried composition comprising a strain of the invention or a formulation of the invention.

The invention also provides a strain or a formulation as described herein for use in foodstuffs.

The invention also provides a strain or a formulation as described herein for use as a medicament.

The invention also provides a strain or a formulation as described herein for use in the prophylaxis and/or treatment of obesity and related illnesses. The invention also provides a strain or a formulation as described herein for use in the prophylaxis and/or treatment of non-alcoholic fatty liver disease (NAFLD).

Strains as described herein may be used in the preparation of a panel of biotherapeutic agents for modifying the levels of IL-10.

The invention also provides a strain or a formulation as described herein for use in the prophylaxis and/or treatment of obesity related inflammation.

The invention also provides a strain or a formulation as described herein for use in the prophylaxis and/or treatment of obesity related metabolic dysregulation.

It will be appreciated that the specific strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition, a vaccine comprising the strains of the invention may be prepared using any suitable known method and may include a pharmaceutically acceptable carrier or adjuvant.

The invention also includes mutants and variants derived from the strain of the invention, whilst still having the activity of the deposited strain. The mutants and variants include a strain whose genetic and/or phenotypic properties are altered compared to the parent strain. A naturally occurring variant includes the spontaneous alterations of targeted properties selectively isolated. Deliberate alteration of parent strain properties is accomplished by conventional (in vitro) genetic manipulation technologies, such as gene disruption, conjugative transfer, etc. Genetic modification includes introduction of exogenous and/or endogenous DNA sequences into the genome of a strain, for example by insertion into the genome of the bacterial strain by vectors, including plasmid DNA, or bacteriophages.

Natural or induced mutations include at least single base alterations such as deletion, insertion, transversion or other DNA modifications which may result in alteration of the amino acid sequence encoded by the DNA sequence.

The terms mutant, variant and genetically modified mutant also include a strain that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism but whose products can be used for identification or selection of the bacterium, for example antibiotic resistance.

A person skilled in the art would appreciate that mutant or variant strains of can be identified by DNA sequence homology analysis with the parent strain. Strains of having a close sequence identity with the parent strain without demonstrable phenotypic or measurable functional differences are considered to be mutant or variant strains. A strain with a sequence identity (homology) of 99.5% or more with the parent DNA sequence may be considered to be a mutant or variant. Sequence homology may be determined using on-line homology algorithm "BLAST" program, publicly available at http://www.ncbi.nlm.nih,gov/BLAST/.

Mutants of the parent strain also include derived strains having at least 95.5% sequence homology to the 16 s-23 s intergenic spacer polynucleotide sequence of the parent strain. These mutants may further comprise DNA mutations in other DNA sequences in the bacterial genome.

BRIEF DESCRIPTION OF THE FIGURES

The invention will be more clearly understood from the following description of some embodiments thereof, given by way of example only, with reference to the accompanying figures, in which.

DETAILED DESCRIPTION OF THE INVENTION

Figure 1:
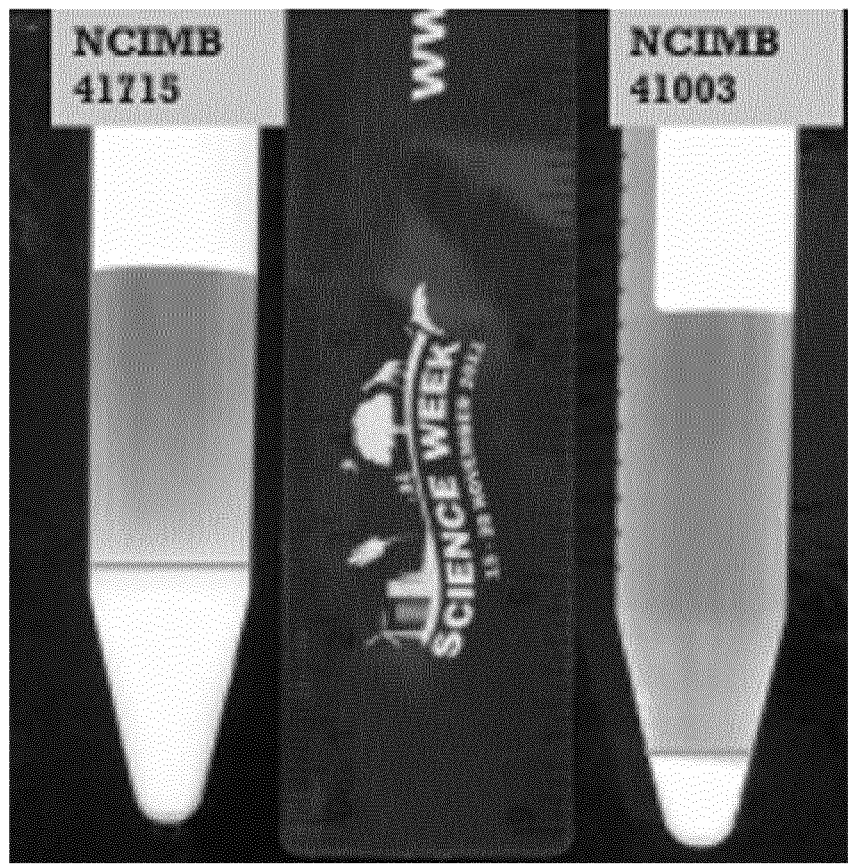
FIG. 1 shows Strain bulkiness of B. longum NCIMB 41715, and B. longum NCIMB 41003 as measured by EPS fluffy pellet height.

A deposit of Bifidobacterium longum AH1362 was made at the National Collections of Industrial and Marine Bacteria Limited (NCIMB) Ferguson Building, Craibstone Estate, Bucksburn, Aberdeen, AB21 9YA, Scotland, UK on May 6, 2010 and accorded the accession number NCIMB 41715.

This specification also makes reference by way of comparison to the strain Bifidobacterium longum 35624 which is deposited at the National Collections of Industrial and Marine Bacteria Limited (NCIMB) Ferguson Building, Craibstone Estate, Bucksburn, Aberdeen, AB21 9YA, Scotland, UK on Jan. 13, 1999 under accession number NCIMB 41003.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

We have found that a novel EPS-producing Bifidobacterium strain (B. longum AH1362) attenuated markers associated with obesity and associated metabolic disorders. B. longum AH1362 administration was associated with alteration of gut microbiota, decreased fat storage and decreased hepatic triglyceride and hepatic total cholesterol levels and increased fat excretion. Surprisingly, administration of B. longum NCIMB 41003 did not have the same effect.

Example 1—Identity of B. longum NCIMB 41715 was Confirmed by BLAST Analysis of the Intergenic Spacer (IGS) Region Method 16 s-23 s intergenic spacer (IGS) sequencing was performed to identify B. longum NCIMB 41715. Briefly, total DNA was isolated from the strains using 100 µl of Extraction Solution and 25 µl of Tissue Preparation solution (Sigma-Aldrich, XNAT2 Kit). The samples were incubated for 5 minutes at room temperature followed by 2 h at 95° C. and then 100 µl of Neutralization Solution (Sigma-Aldrich, XNAT2 kit) was added. DNA solution was quantified using a Nanodrop spectrophotometer and stored at 4° C. PCR was performed using the IGS primers. The primer pairs used for identification of the both strain were IGS R 5'-CTGGTGC-CAAGGCATCCA-3' and IGS L 5'-GCTGGAT-CACCTCCTTTCT-3'. The cycling conditions were 94° C. for 4 min (1 cycle), 94° C. for 45 sec, 53° C. for 45 sec, 72°

C. for 45 sec (28 cycles). The PCR reaction contained 2 µl (100 ng) of DNA, PCR mix (Sigma-Aldrich, Red Taq), 0.025 nM IGS L and R primer (MWG Biotech, Germany). The PCR reactions were performed on an Eppendorf thermocycler. The PCR products were run alongside a molecular weight marker (100 bp Ladder, Roche) on a 2% agarose EtBr stained gel in TAE, to determine the IGS profile. PCR products of Bifidobacterium (single band) were purified using the Promega Wizard PCR purification kit. PCR products of Lactobacillus yield 3 bands. The band present at approx. 280 bp (lowest band) was excised, purified using the GenElute Agarose Spin Column (Sigma-Aldrich) and re-sequenced as above and the PCR product was purified using the Promega Wizard PCR purification kit. The purified PCR products were sequenced at Beckman Coulter Genomics (UK) using the primer sequences (above) for the intergenic spacer region. Sequence data was then searched against the NCBI nucleotide database to determine the identity of the strain by nucleotide homology. The resultant DNA sequence data was subjected to the NCBI standard nucleotide-to-nucleotide homology BLAST search engine (http://www.ncbi.nlm.nih.gov/BLAST/) to identify the nearest match to the sequence.

Results

TABLE 1

Blast results of the intergenic spacer (IGS) region of B. longum NCIMB 41715.

| Sample | Accession no | Closest Match on NCBI BLAST Jul. 12, 2015 | Identities | % Match | bp |
|---|---|---|---|---|---|
| NCIMB 41715 | gb(CP010453.1) | Bifidobacterium longum strain BG7, complete genome | 480/484 | 99% | 495 |
|  | emb(LN824140.1) | Bifidobacterium longum subsp, infantis genome assembly |  |  |  |

TABLE 2

Sequence of the intergenic spacer (IGS) region of B. longum NCIMB 41715.

```
IGS         TGCTGGGATCACCTCCTTTCTACGGAGAATTCAGTCGGATG
sequence    TTCGTCCGACGGTGTGCGCCCCGCGCGTCGCATGGTGCG
of B.       ATGGCGGCGGGGTTGCTGGTGTGGAAGACGTCGTTGGCTTT
longum      GCCCTGCCGGTCGTGCGGTGGGTGCGGGTGGTATGGAT
NCIMB       GCGCTTTTGGGCTCCCGGATCGCCACCCCAGGCTTTTTGCC
41715       TGGCGCGATTCGATGCCCGTCGTGCCTGGGGGCCGGCCG
(495 nt)    TGTGCCGGCGCGATGGCGTGGCGGTGCGTGGTGGCTTGAGA
            ACTGGATAGTGGACGCGAGCAAAACAAGGGTTTTTGAAT
            CTTTGTTTTGCTGTTGATTTCGAATCGAACTCTATTGTTCG
            TTTCGATCGTTTTGTGATCATTTTTAGTGTGATGATTTG
            TCGTCTGGGAATTTGCTAGAGGAATACTTGCGGCCATGCAC
            TTCGTGGTGTGTGTTGCTTGCAAGGGCGTATGGTGGAGG
            CCTTCGACCACCAGA
```

Example 2—EPS Fluffy Pellet Test (Strain Bulkiness)

Method

Each strain was fermented in a broth. The particulate collected after centrifugation was washed and subsequently freeze dried.

The freeze-dried powder, adjusted for total cell number (2×10E10), was re-suspended in 10 ml PBS and centrifuged at 4000 rpm/10 mins/4° C.

Results

FIG. 1: Strain bulkiness of B. longum NCIMB 41715 and B. longum NCIMB 41003 as measured by EPS fluffy pellet height.

B. longum NCIMB 41003 produced a 0.9 cm fluffy pellet while. B. longum NCIMB 41715 produced a 2.5 cm fluffy pellet Conclusion B. longum NCIMB 41003 is known to be a high EPS producer. The EPS fluffy pellet test, and the resulting pellet height, confirms that B. longum NCIMB 41715 produces EPS, and produces more EPS than B. longum NCIMB 41003.

Example 3—Microbial Adhesion to Hexadecane (MATH) Assay

Hydrophobicity is the physical property of a molecule whereby it repels water. Hydrophobic materials are used for oil removal from water, the management of oil spills, and chemical separation processes to remove non-polar substances from polar compounds. Hydrophobicity of a bacterial cell depends on the composition of its cell surface with respect to the proteins, peptides and polysaccharides present. The ability of a probiotic strain to adhere to the intestinal mucosa helps the bacterial cell to establish itself during gastrointestinal transit providing it with a competitive advantage in the intestine. Hydrophobicity of a strain is one factor contributing to adhesive ability. The determination of bacterial adhesion to hexadecane as an indication of the strains ability to adhere to intestinal epithelial cells is a valid qualitative approach (Kiely & Olson, 2000).

Method

The ability of B. longum NCIMB 41715 and B. longum NCIMB 41003 to adhere to hexadecane as a measure of their hydrophobicity was determined using the microbial adhesion to hexadecane (MATH) test. Adhesion to hexadecane was measured according to the method of Rosenberg el al, 1980 with some modifications (Crow and Gopal, 1995; Bellon-Fontaine el al, 1996). Bacteria were harvested in the stationary phase by centrifugation at 5000 g for 15 min, washed twice with PBS, and re-suspended in 0.1 mol/l $KNO_3$ (pH 6.2) to an $OD_{600}$ of 0.8. The absorbance of the cell suspension was measured at 600 nm (A0). 2 ml of hexadecane (Sigma Aldrich) was added to 2 ml of cell suspension. After 10 min pre-incubation at room temperature, the two-phase system was mixed by vortexing for 2 mins. The aqueous phase was removed after 20 min of incubation at room temperature, and its absorbance at 600 nm (A1) was measured. The % of bacterial adhesion to hexadecane was calculated as $(1-A1/A0) \times 100$, where A0 and A1 are the absorbance before and after extraction with the solvents, respectively. Experiments were done in triplicate with cells coming from independent cultures.

Results

Figure 2:
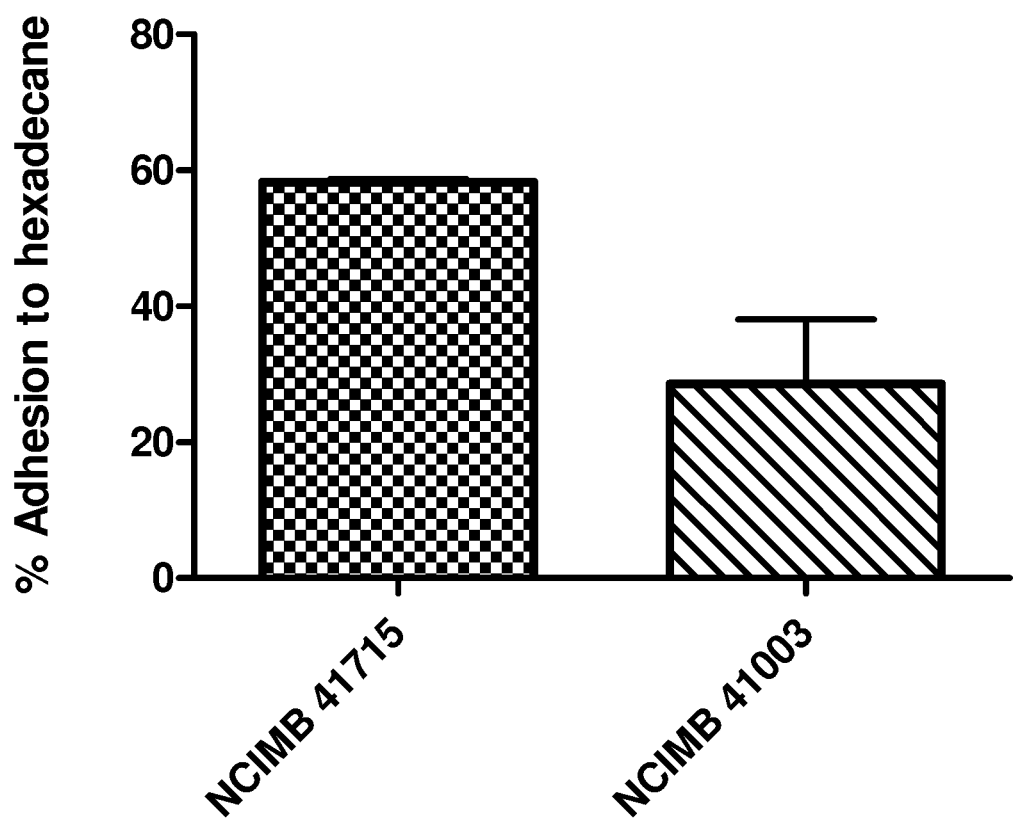
FIG. 2 is a bar chart of % adhesion to hexadecane of B. longum NCIMB 41715, and B. longum NCIMB 41003.

FIG. 2: % adhesion of B. longum NCIMB 41715 and B. longum NCIMB 41003 to hexadecane as a measure of their hydrophobicity.

Conclusion

B. longum NCIMB 41715 (58.3%) showed a higher affinity for hexadecane, indicating that it had greater hydrophobicity, in comparison to B. longum NCIMB 41003 (28.6%).

Example 4—PBMC Anti-Inflammatory Profiles

The anti-inflammatory profile of B. longum NCIMB 41715, B. longum NCIMB 41003 and a low EPS producing Lactobacillus strain were examined by assessing the induction of the anti-inflammatory cytokine IL-10 and the pro-inflammatory cytokine TNF-α in the peripheral blood mononuclear cell (PBMC) cytokine induction assay.

Method

Peripheral Blood Mononuclear Cell (PBMC) Cytokine Induction Assay

Blood was obtained from three healthy volunteers under approval of the Clinical Research Ethics Committee of the Cork Teaching Hospitals. Subjects were all and had abstained from probiotic, antibiotic or anti-inflammatory medication usage for one month or longer prior to blood donation. PBMCs were extracted from whole blood by density gradient separation using histopaque (Sigma-Aldrich), a hydrophilic polysaccharide that separates layers of blood, with a 'buffy coat' forming under a layer of plasma which contains the PBMCs. For each strain, 100 mg of freeze-dried powder was weighed out and re-suspended in sterile Dulbecos PBS (Sigma-Aldrich). The bacterial cells were washed twice by centrifugation (4000 rpm/10 min/4° C./Brake 0) and re-suspended in sterile PBS. Direct microscopic counts were performed and the cell preparations were diluted to the appropriate concentrations to give a ratio of 100:1; 50:1; 25:1 total bacteria: PBMC cells. Technical replicates were performed in triplicate. PBMCs were then incubated at a concentration of $2\times10^5$ cells/ml for 48 h at 37° C. (in the presence of penicillin and streptomycin (Sigma-Aldrich)) with control media, or with increasing concentrations of the bacterial strains: $1\times10^6$ cells/ml (25:1 Bacterial: PBMC), $1\times10^7$ cells/ml (50:1 Bacteria:PBMC) and $2\times10^7$ cells/mL (100:1 Bacteria:PBMC). Supernatants were assayed for the anti-inflammatory cytokine IL-10 and the pro-inflammatory cytokine TNF-α which were measured using the MesoScale Discovery (MSD) multiplex platform tissue culture kits (Meso Scale Diagnostics, Maryland, USA). B. longum NCIMB 41003, which has previously been shown to have anti-inflammatory activity (Groeger el al., 2013) was used as a positive control to validate the accuracy of the assay.

Results

Figure 3:
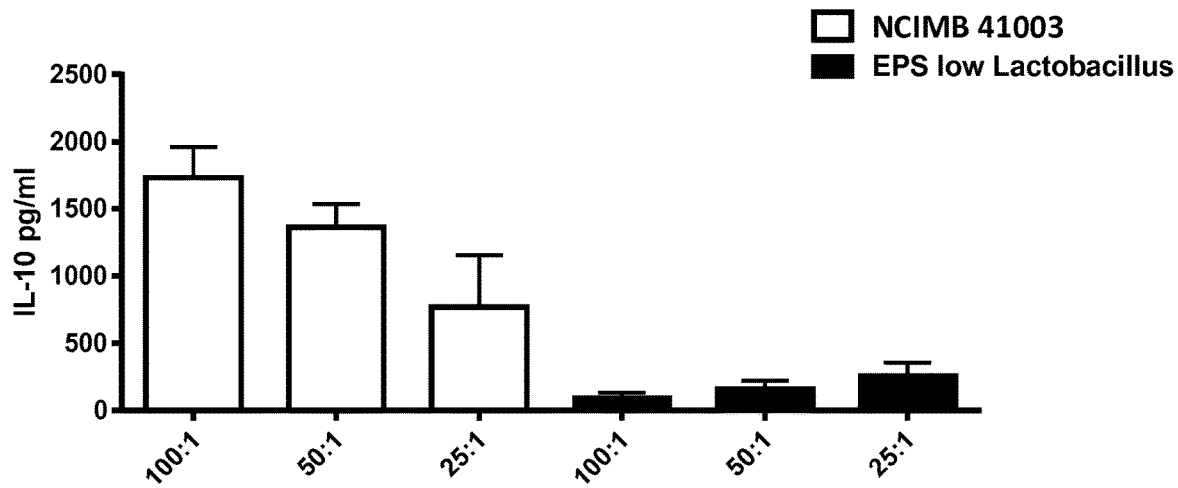
FIG. 3 is a chart of IL-10 induction in the PBMC cytokine induction assay following 48 h stimulation with the EPS+ve B. longum NCIMB 41003 and a low EPS producing Lactobacillus strain. There is an enhanced induction of the anti-inflammatory cytokine IL-10 following stimulation with the EPS+ve B. longum NCIMB 41003 relative to the EPS low Lactobacillus strain.

FIG. 3: IL-10 induction in the PBMC cytokine induction assay following 48 h stimulation with the EPS+ve B. longum NCIMB 41003 and a low EPS producing Lactobacillus strain. There is an enhanced induction of the anti-inflammatory cytokine IL-10 following stimulation with the EPS+ve B. longum NCIMB 41003 relative to the EPS low Lactobacillus strain.

Figure 4:
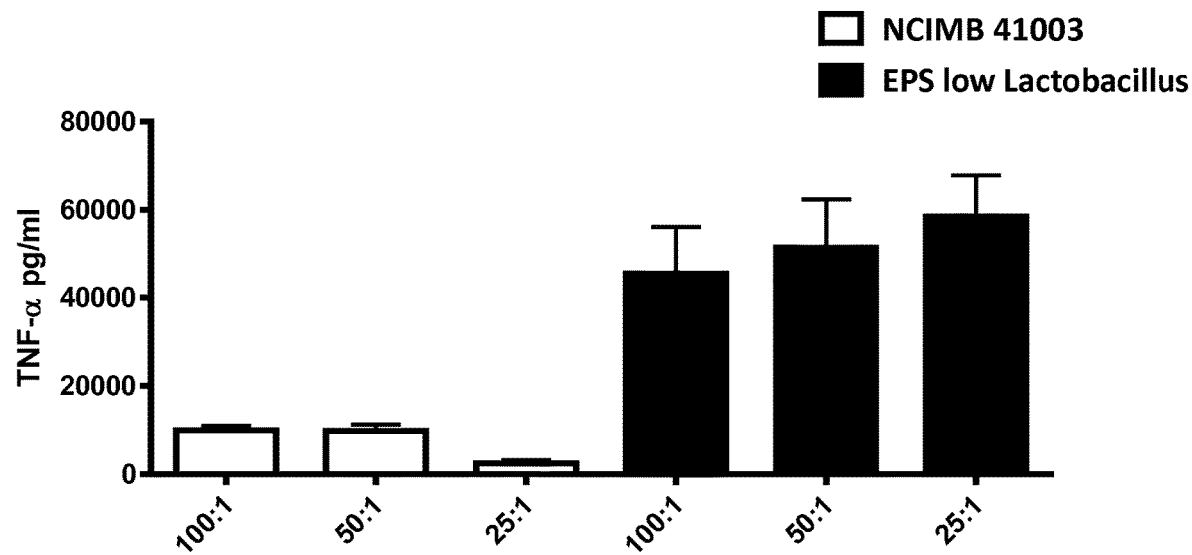
FIG. 4 is a chart of TNF-α induction in the PBMC cytokine induction assay following 48 h stimulation with B. longum NCIMB 41003 and a low EPS producing Lactobacillus strain. There is a decreased induction of the pro-inflammatory cytokine TNF-α induction following stimulation with the EPS+ve B. longum NCIMB 41003 relative to the EPS low Lactobacillus strain.

FIG. 4: TNF-α induction in the PBMC cytokine induction assay following 48 h stimulation with B. longum NCIMB 41003 and a low EPS producing Lactobacillus strain. There is a decreased induction of the pro-inflammatory cytokine TNF-α induction following stimulation with the EPS+ve B. longum NCIMB 41003 relative to the EPS low Lactobacillus strain.

Figure 5:
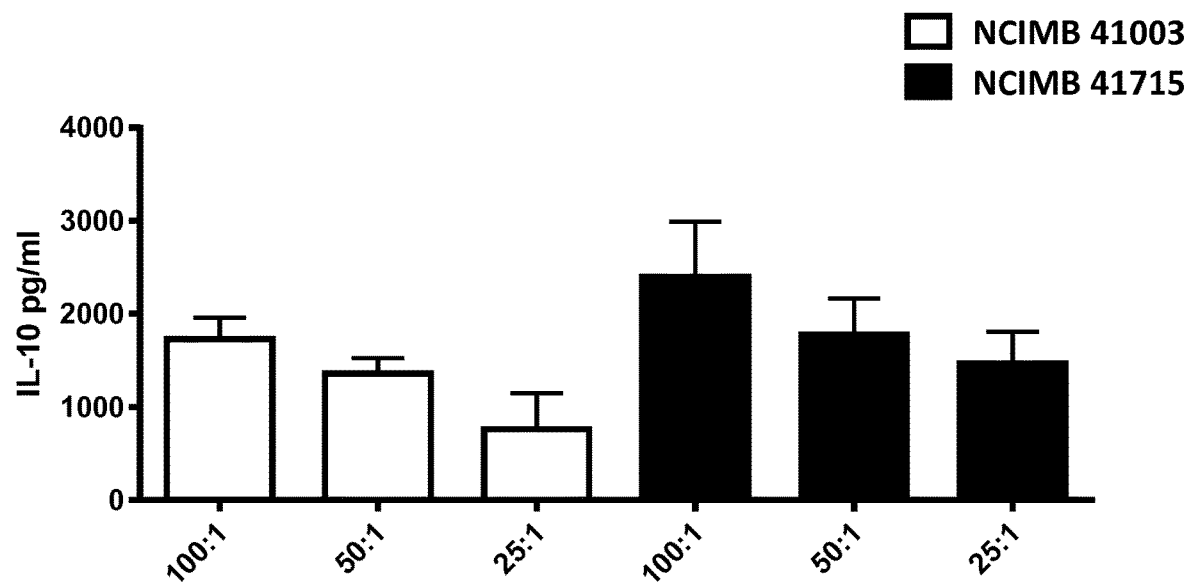
FIG. 5 is a chart of IL-10 induction in the PBMC cytokine induction assay following 48 h stimulation with B. longum NCIMB 41003 and B. longum NCIMB 41715. Both strains induce, in a dose responsive manner, similar levels of the anti-inflammatory cytokine IL-10.

FIG. 5: IL-10 induction in the PBMC cytokine induction assay following 48 h stimulation with B. longum NCIMB 41003 and B. longum NCIMB 41715. Both strains induce, in a dose responsive manner, similar levels of the anti-inflammatory cytokine IL-10.

Figure 6:
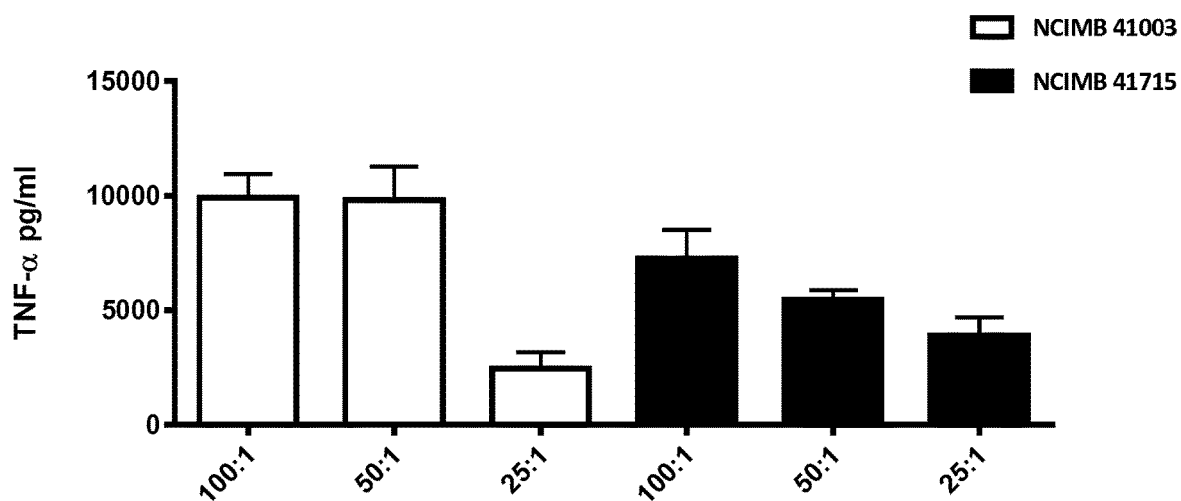
FIG. 6 is a chart of TNF-α induction in the PBMC cytokine induction assay following 48 h stimulation with B. longum NCIMB 41003 and B. longum NCIMB 41715. B. longum NCIMB 41715 induce similar levels of TNF-α relative to B. longum NCIMB 41003.

FIG. 6: TNF-α induction in the PBMC cytokine induction assay following 48 h stimulation with B. longum NCIMB 41003 and B. longum NCIMB 41715. B. longum NCIMB 41715 induce similar levels of TNF-α relative to B. longum NCIMB 41003.

Conclusion

B. longum NCIMB 41715 and B. longum NCIMB 41003, which are EPS-rich, induce similar anti-inflammatory immune profiles in a PBMC cytokine induction assay. The low-EPS producing strain produces a very different immune profile.

Example 5—Effect of Administration of B. longum NCIMB 41715, B. longum NCIMB 41003 and an EPS Low Lactobacillus Strain on Metabolic Outcomes in the Diet-Induced Obesity (DIO) Mouse Model Method Animals 7-week-old male C57BL/6JRccHsd mice (Harlan Laboratories, Netherlands) (72 mice, n=12 per group), randomized based on body weight, were maintained in a controlled environment with 22±3° C. temperature, 50±20% humidity, a light/dark cycle of 12 h each and 15-20 fresh air changes per hour. Mice were housed group wise (4 mice per cage) and autoclaved corncob was used as bedding material. Mice were received at 5 weeks of age and were quarantined for one week followed by acclimatization for one week prior to commencement of study. From Day 0 mice were fed, ad libitum, and mice in each cage were provided with 50 ml of plain sterile drinking water (groups 1 and 2; Table 1) or drinking water containing freeze-dried probiotic ($1\times10^9$ cfu/dose/day) via polycarbonate bottles fitted with stainless steel sipper tubes (groups 3, 4, 5 and 6; Table 1). Treatment continued for 16 weeks.

Experimental Design

Day 0 onwards, group 1 was fed with low fat diet (LFD) D12450 (10% kcal % fat, gamma irradiated; Research Diets Inc, USA) and the other five groups (groups 2 to 6) were fed with high fat diet (HFD) D12451 (45% kcal % fat, gamma irradiated; Research Diets Inc) for a period of 16 weeks. HFD feeding induced insulin resistance and obesity in animals which was characterized by increase in body weight and fasting blood glucose values. Group 1 and 2 were provided with plain sterile drinking water while groups 3, 4, 5 and 6 were provided with drinking water containing $1\times10^9$ cfu/dose/day of the appropriate probiotic (Table 1). General health observation was performed on a daily basis at the same time of the day. This included alertness, hair texture, cage movement and presence of any discharge from nose, eyes, mouth and ears. Pre-measured feed was kept in each cage and the left-over feed was measured and recorded on every third day to access the amount of food consumed by the mice. Water consumption of the animals was measured on a daily basis starting from the first dosing day. Mice in each cage (n=4) were provided with 50 mL of water daily. The remaining water in each cage was measured every 24 h.

Weights and Tissue Sampling

Body weights were recorded individually for all animals at receipt, day of randomization, prior to treatment, and once in three days thereafter. The percent change in bodyweight was calculated according to the formula (TT-TC)/TC*100 where TT is the test day treated and TC is the test day control. Mice were subjected to Echo Magnetic Resonance Imaging (MRI) using an Echo MRI (EchoMRI-700™) on day −1 and 28, 56, 84 and 112 to assess body fat and lean mass composition. The animal was placed in a plastic holder without sedation or anaesthesia. Fat is measured as the mass of all the fat molecules in the body. Lean is a muscle tissue mass equivalent of all the body parts containing water. Contribution to "free water" comes mostly from the bladder. Total water includes both the free water and the water contained in lean mass, which is the entire water content of the body. Plastic holders were sanitized between animals from different groups to avoid cross-contamination. Aseptic technique was followed while handling animals from different groups. At the end of week 16, the animals were sacrificed by $CO_2$ asphyxiation. Liver, skeletal muscle, visceral fat (epididymal, renal and mesenteric), subcutaneous fat, spleen, caecum, brown adipose fat, brain and intestine were collected, weighed and stored at −80° C. for future biochemical and genetic analysis.

Metabolic Markers

Blood samples were collected at morning 9 am by the tail nipping method on day 0, 30, 60, 90 and 112 for random blood glucose measurements (total 5 samplings were done), starting/including the first dosing day. Blood glucose analysis was done by Johnson and Johnson glucometer (One touch Ultra 2). Aseptic technique was followed while handling animals from different groups. At the end of 16 weeks, mice were fasted for 6 h and blood was collected by the tail nipping method (non-anesthetic mode of blood collection) for blood glucose estimation. Blood was collected by retro-orbital puncture method under light isoflurane anesthesia and plasma was separated which was used for estimating total cholesterol (TC), triglycerides (TG), high-density lipoprotein (HDL) cholesterol, low-density lipoprotein (LDL) cholesterol and non-esterified fatty acids (NEFA) by fully automated random access clinical chemistry analyzer (EM-360, Erba Mannheim, Germany). Plasma VLDL levels were obtained by the calculation method: (VLDL=Triglycerides (mg/dl)/5). For hepatic TC and TG estimation, liver was homogenized in isopropanol (1 ml/50 mg tissue) and incubated at 4° C. for 1 h. The samples were centrifuged at 4° C. for 5 min at 2,500 rpm. Cholesterol and triglyceride concentrations in the supernatants were measured by a fully automated random access clinical chemistry analyzer (EM-360, Erba Mannheim).

Energy Excretion Estimation

Two faecal pellets were collected from each mouse at Weeks 6, 10 and 15 and analyzed for their gross calorific value by bomb calorimetry. For bomb calorimetry analysis, the samples were weighed and oven-dried at 60° C. for 48 h. The energy content of the faeces was assessed with a Parr 6100 calorimeter using an 1109 semi-micro bomb (Parr Instruments & Co., Moline, Ill., USA). The calorimeter energy equivalent factor was determined using benzoic acid standards and each sample (100 mg) was analysed in triplicate. Cumulative energy excretion of probiotic fed mice over the course of the study was estimated as a percentage relative to energy excreted by mice from the high-fat diet control group.

Statistical Analysis

Statistical analysis was performed using unpaired t-test for differences between two groups. One-way analysis of variance (ANOVA), followed by Tukey's multiple comparison test was used when more than two groups were assessed. Data were analyzed using GraphPad Prism version 5.00 for Windows (GraphPad Software). The results were considered statistically significant when $p<0.05$.

TABLE 5

Experimental groups and associated diet and treatment regimens. LFD = Low fat diet control; HFD = high-fat diet control.

| Groups | Number of mice/group | Diet regimen | Treatment regimen |
|---|---|---|---|
| Group 1 (LFD control) | 12 | 10% fat kcal | Plain sterile drinking water, daily |
| Group 2 (HFD control) | 12 | 45% fat kcal | Plain sterile drinking water, daily |
| Group 4 (HFD + EPS low *Lactobacillus* strain) | 12 | 45% fat kcal | $1 \times 10^9$ cfu/dose/day in drinking water, daily |
| Group 5 (HFD + *B. longum* NCIMB 41715) | 12 | 45% fat kcal | $1 \times 10^9$ cfu/dose/day in drinking water, daily |
| Group 6 (HFD + *B. longum* NCIMB 41003) | 12 | 45% fat kcal | $1 \times 10^9$ cfu/dose/day in drinking water, daily |

Results

Figure 7:
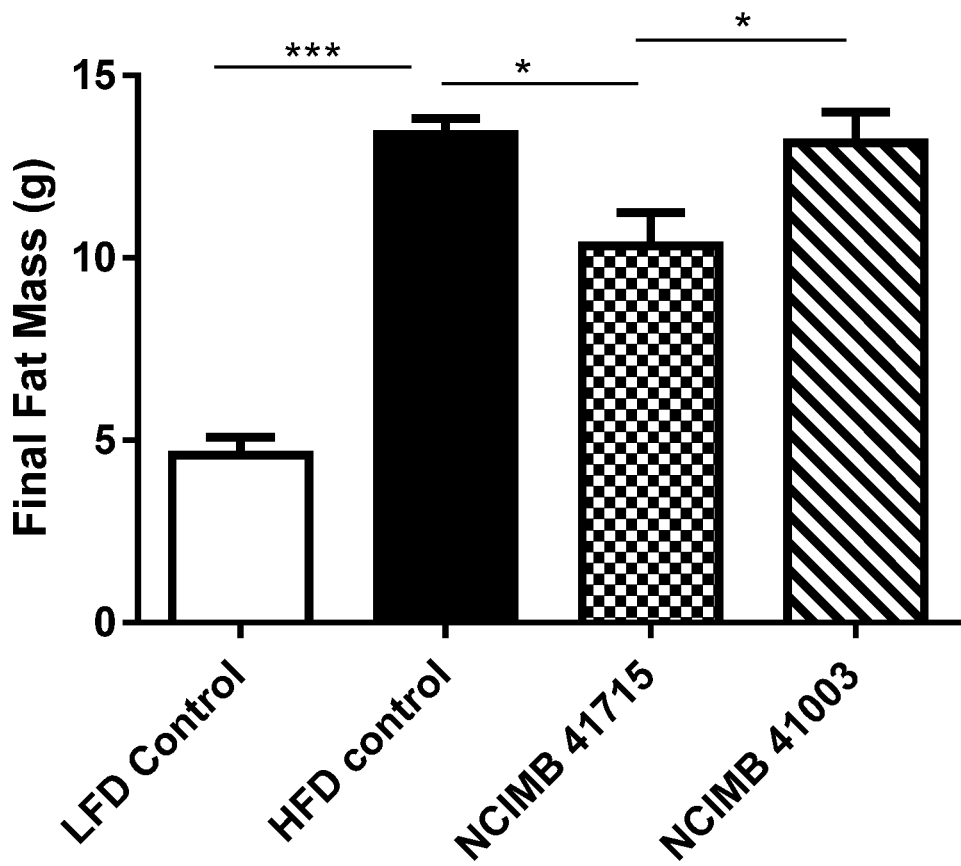
FIG. 7 shows that when compared to the high-fat diet (HFD) control group, B. longum NCIMB 41715 showed a significant reduction of fat mass gain by week 16 while B. longum NCIMB 41003 had no significant effect.

FIG. 7: When compared to the high-fat diet (HFD) control group, *B. longum* NCIMB 41715 showed a significant reduction of fat mass gain by week 16 while *B. longum* NCIMB 41003 had no significant effect.

Figure 8:
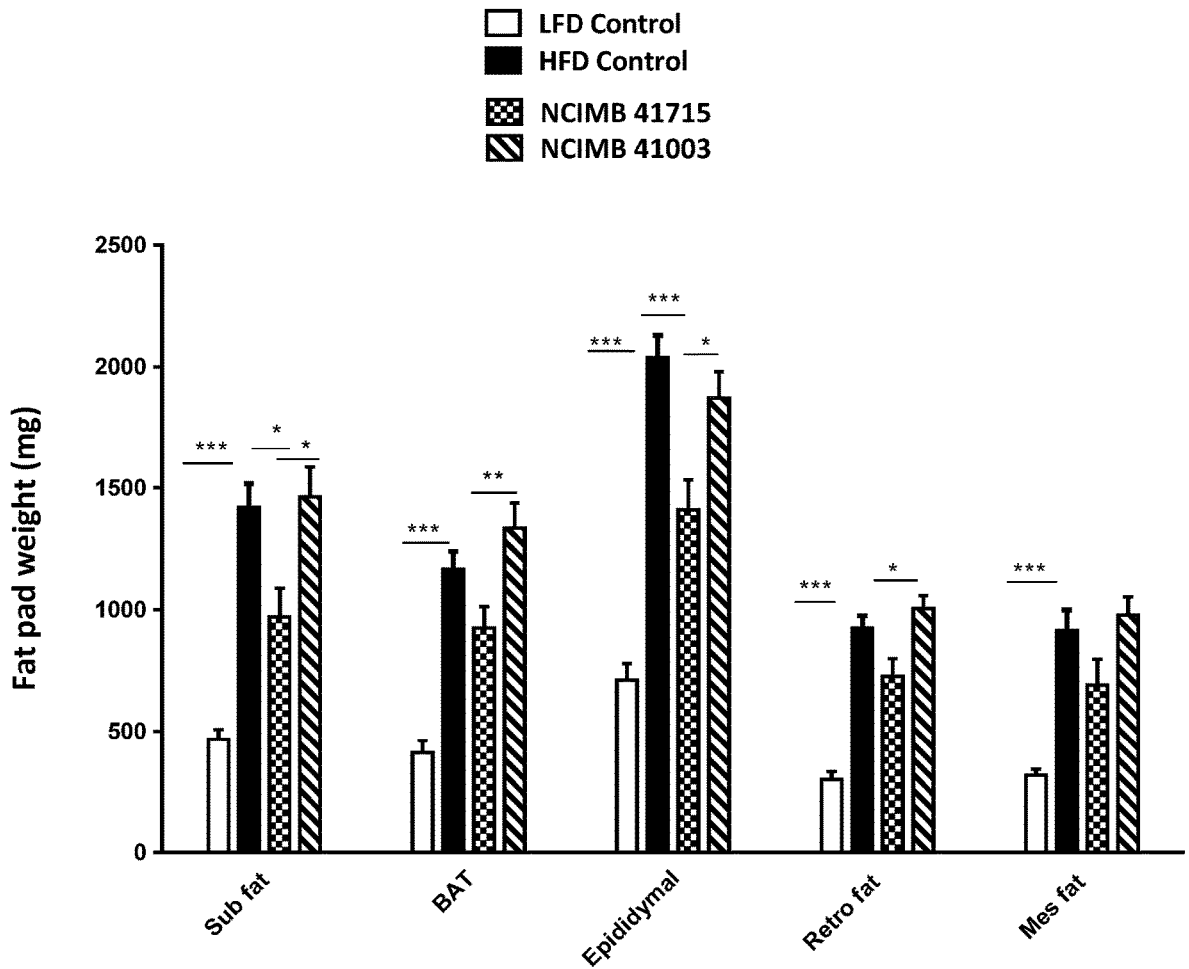
FIG. 8 illustrates the effect of B. longum NCIMB 41715 and B. longum NCIMB 41003 on fat pad weight. B. longum NCIMB 41715 had a significant reduction in fat pad weights (subcutaneous fat and epipidymal fat) while B. longum NCIMB 41003 had no significant effect.

FIG. 8: Effect of *B. longum* NCIMB 41715 and *B. longum* NCIMB 41003 on fat pad weight. *B. longum* NCIMB 41715 had a significant reduction in fat pad weights (subcutaneous fat and epididymal fat) while *B. longum* NCIMB 41003 had no significant effect.

Figure 9:
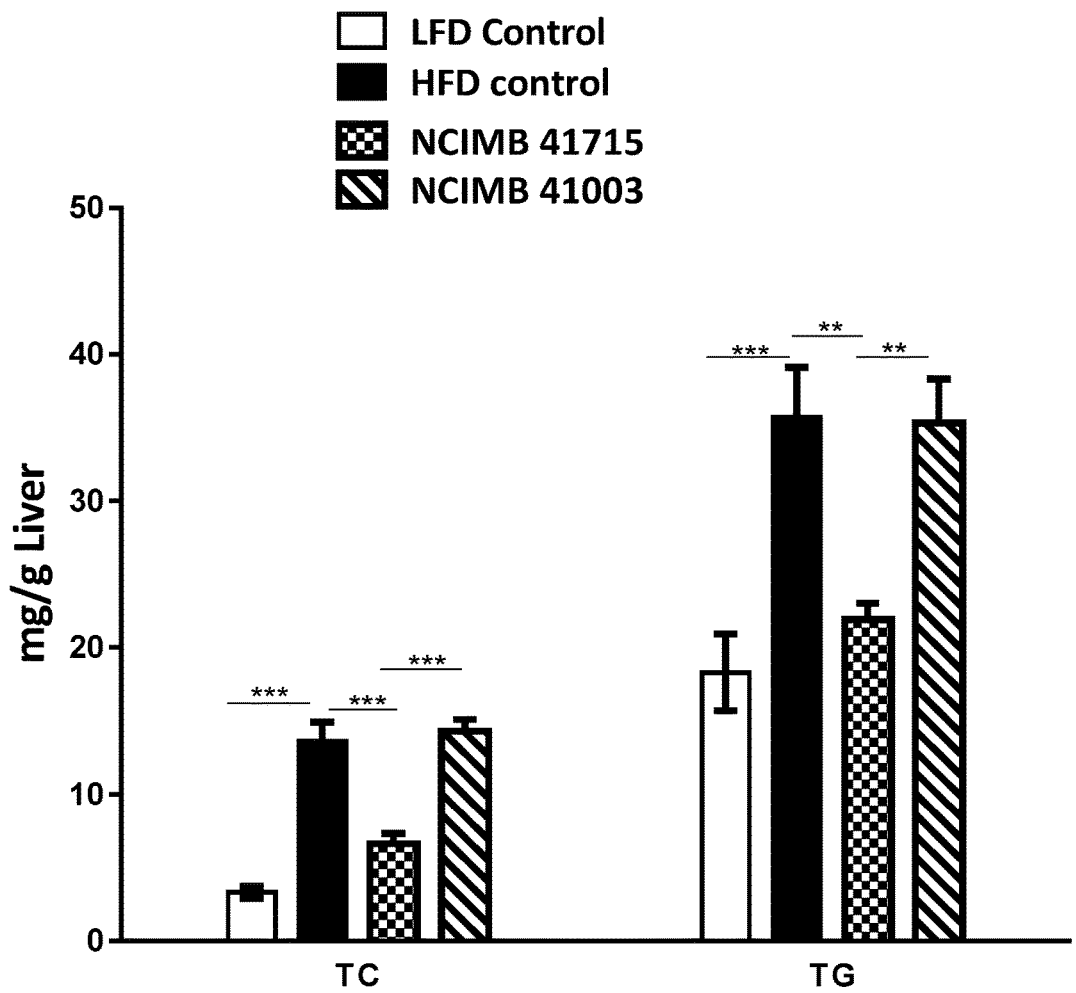
FIG. 9 illustrates the effect of B. longum NCIMB 41715 and B. longum NCIMB 41003 on hepatic total cholesterol and triglycerides. B. longum NCIMB 41715 but not B. longum NCIMB 41003 reduced hepatic total cholesterol and triglycerides in DIO mice.

FIG. 9: Effect of *B. longum* NCIMB 41715 and *B. longum* NCIMB 41003 on hepatic total cholesterol and triglycerides. *B. longum* NCIMB 41715 but not *B. longum* NCIMB 41003 reduced hepatic total cholesterol and triglycerides in DIO mice.

Figure 10:
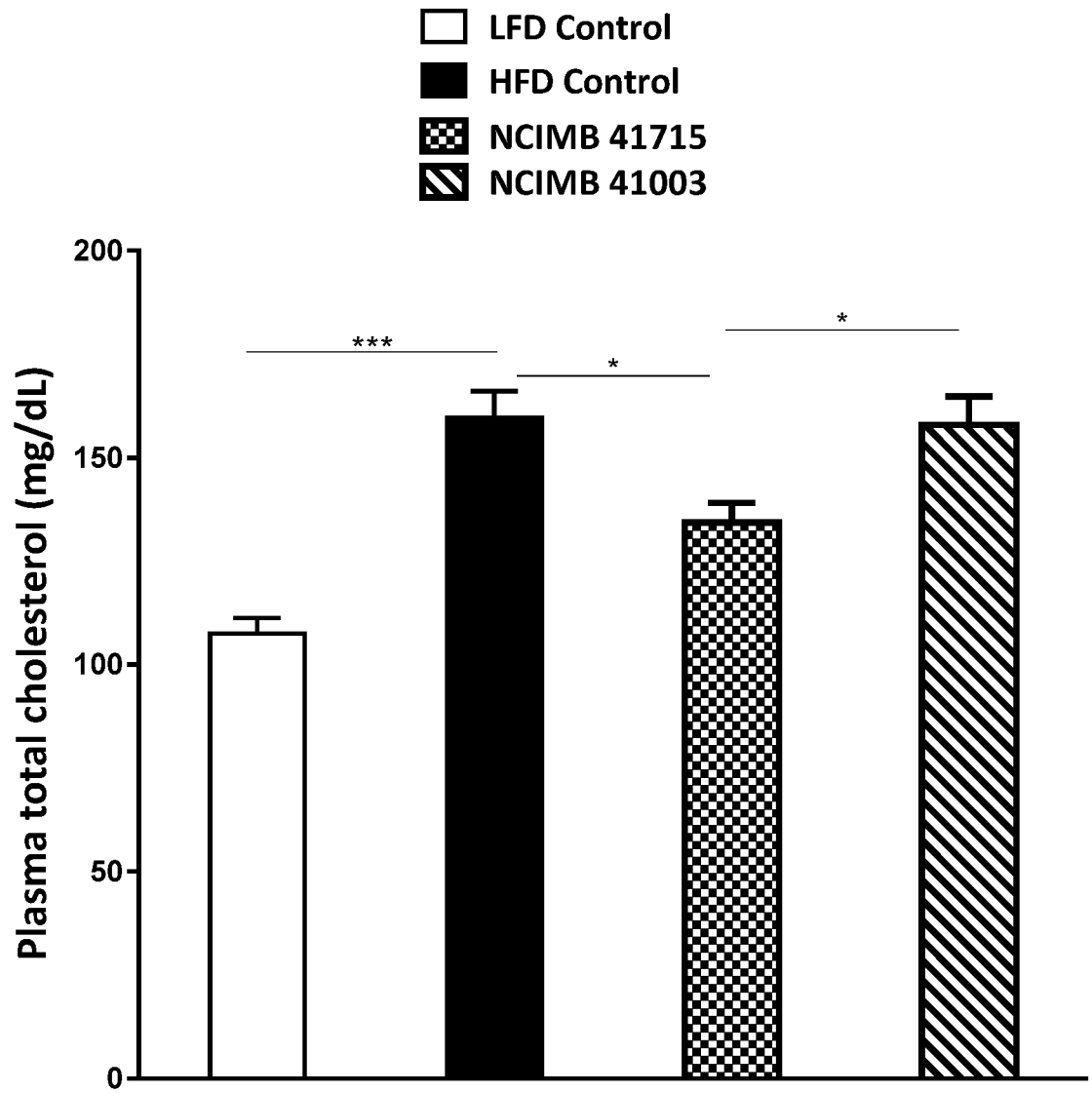
FIG. 10 illustrates the effect of B. longum NCIMB 41715 and B. longum NCIMB 41003 on plasma total cholesterol.

FIG. 10: Effect of *B. longum* NCIMB 41715 and *B. longum* NCIMB 41003 on plasma total cholesterol.

Figure 11:
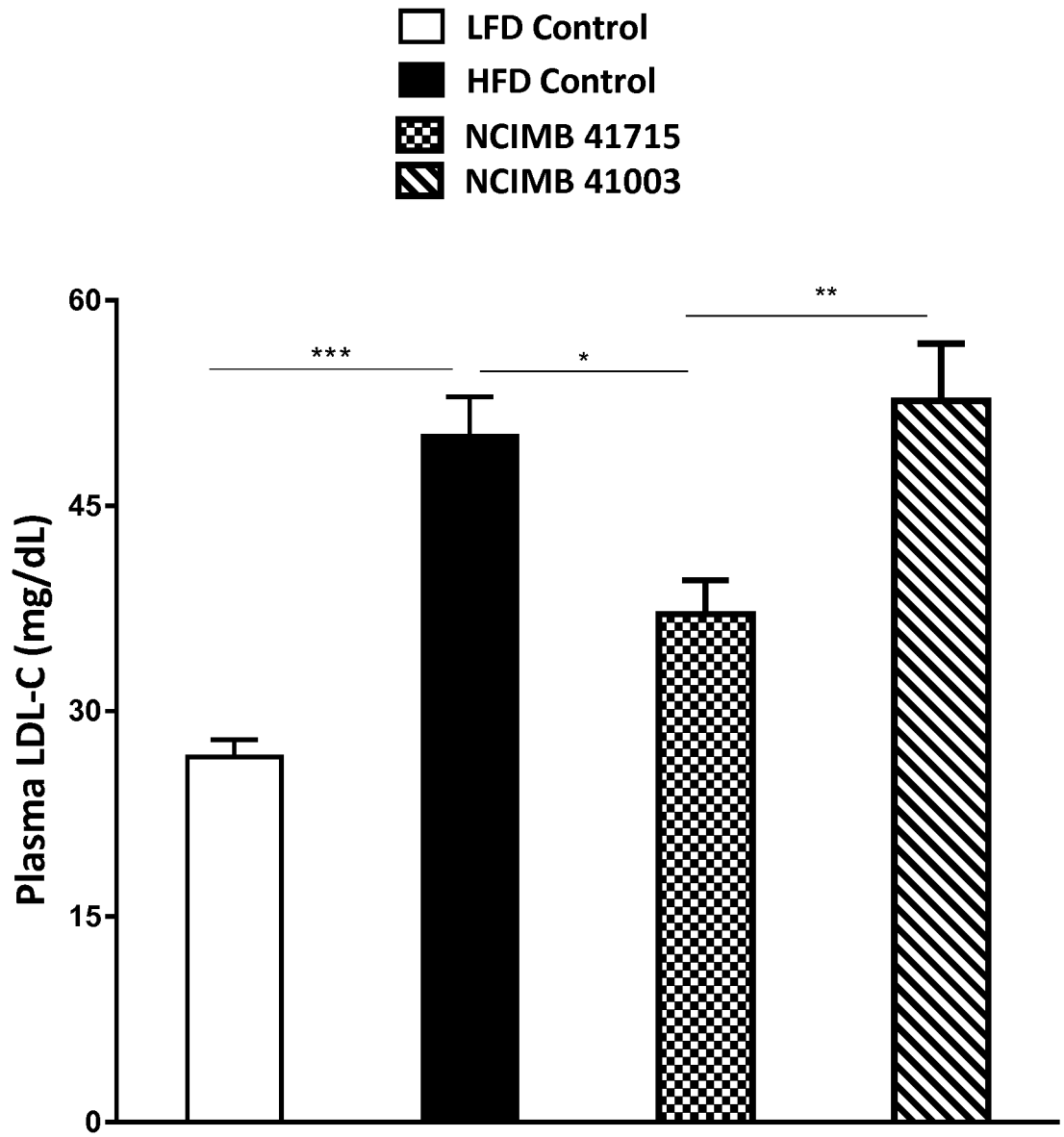
FIG. 11 illustrates the effect of B. longum NCIMB 41715 and B. longum NCIMB 41003 on plasma LDL-cholesterol.

FIG. 11: Effect of *B. longum* NCIMB 41715 and *B. longum* NCIMB 41003 on plasma LDL-cholesterol.

Figure 12:
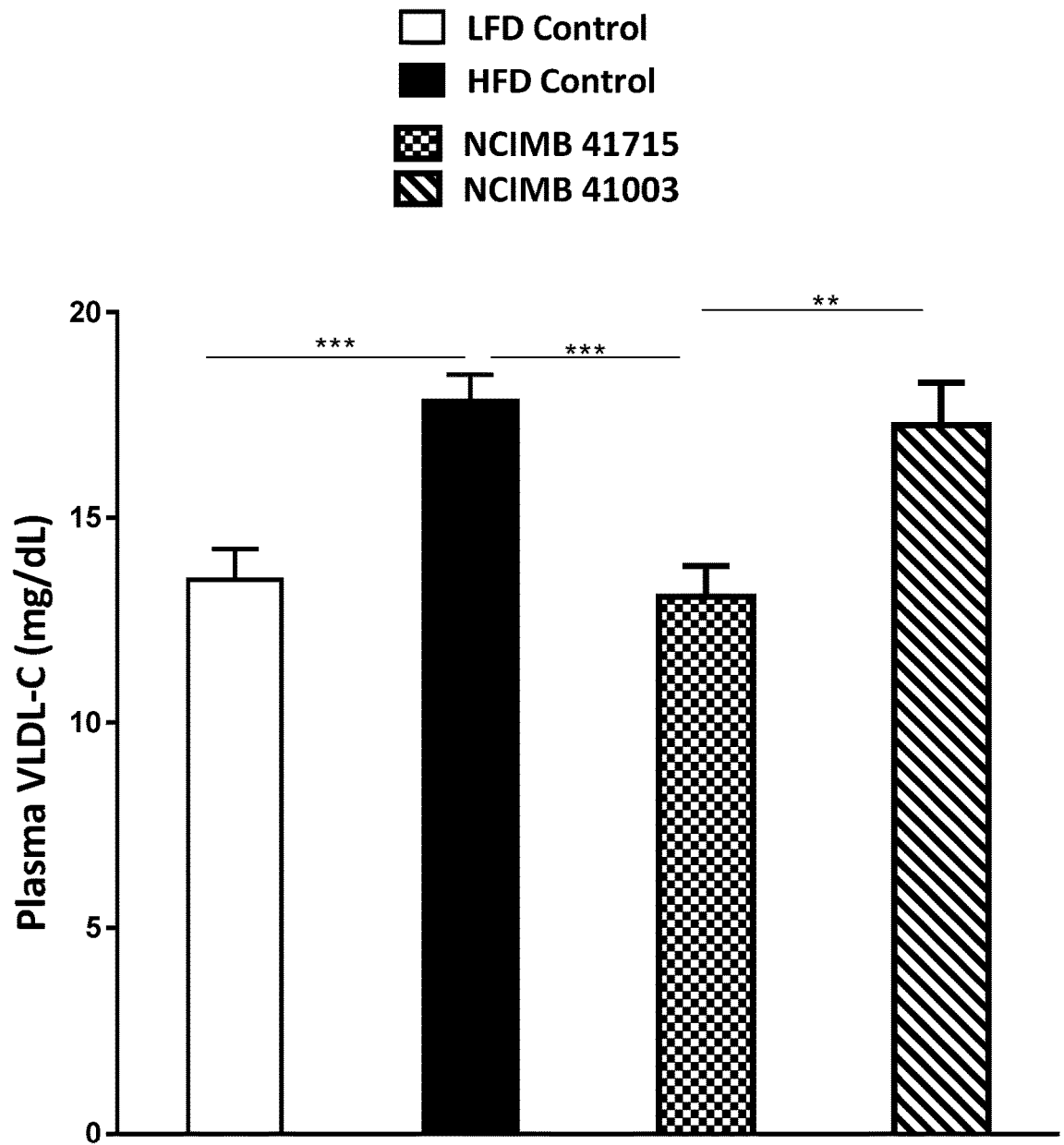
FIG. 12 illustrates the effect of B. longum NCIMB 41715 and B. longum NCIMB 41003 on plasma VLDL-cholesterol.

FIG. 12: Effect of *B. longum* NCIMB 41715 and *B. longum* NCIMB 41003 on plasma VLDL-cholesterol.

Figure 13:
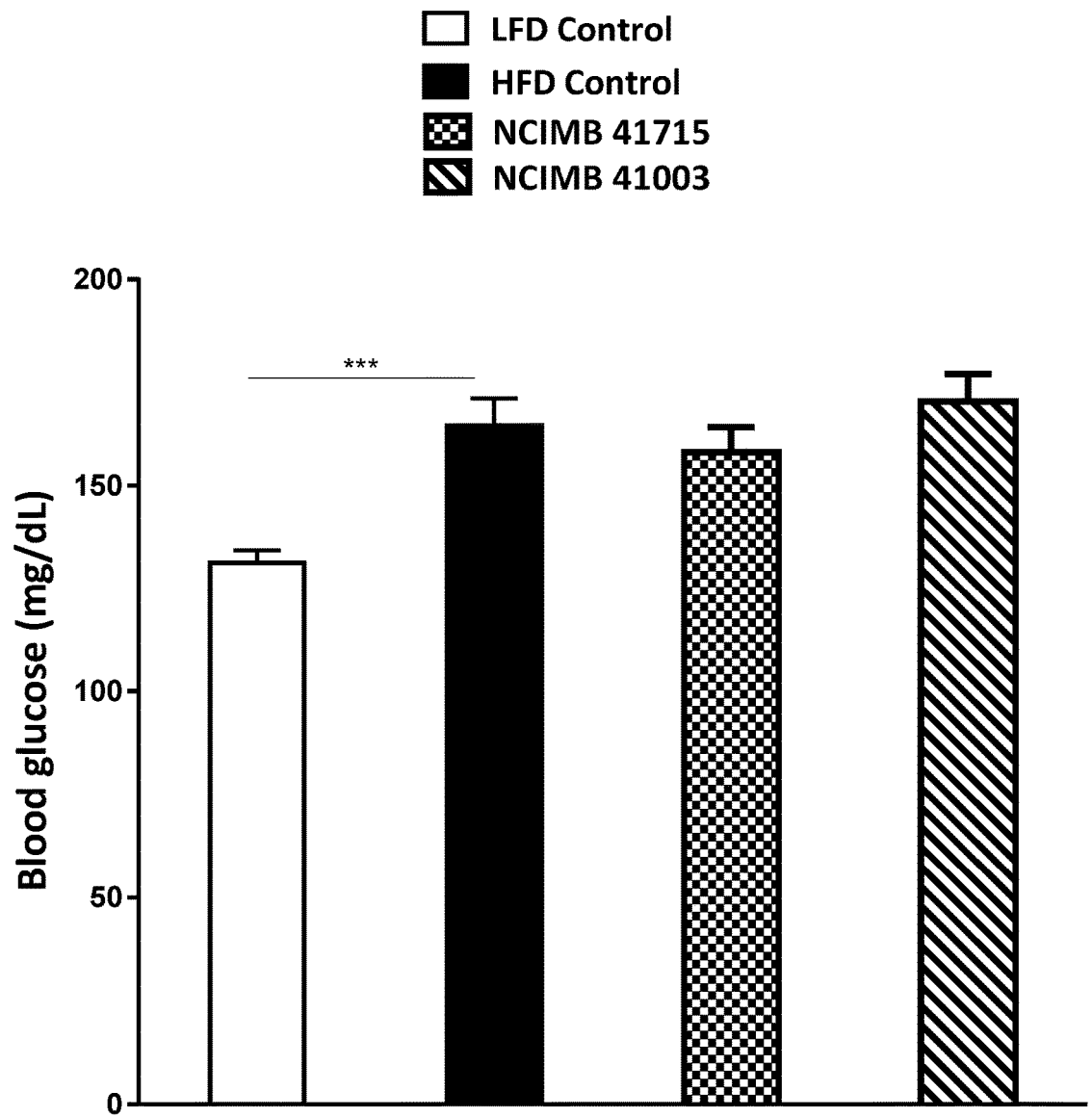
FIG. 13 illustrates the effect of B. longum NCIMB 41715 and B. longum NCIMB 41003 on terminal blood glucose.

FIG. 13: Effect of *B. longum* NCIMB 41715 and *B. longum* NCIMB 41003 on terminal blood glucose.

Figure 14:
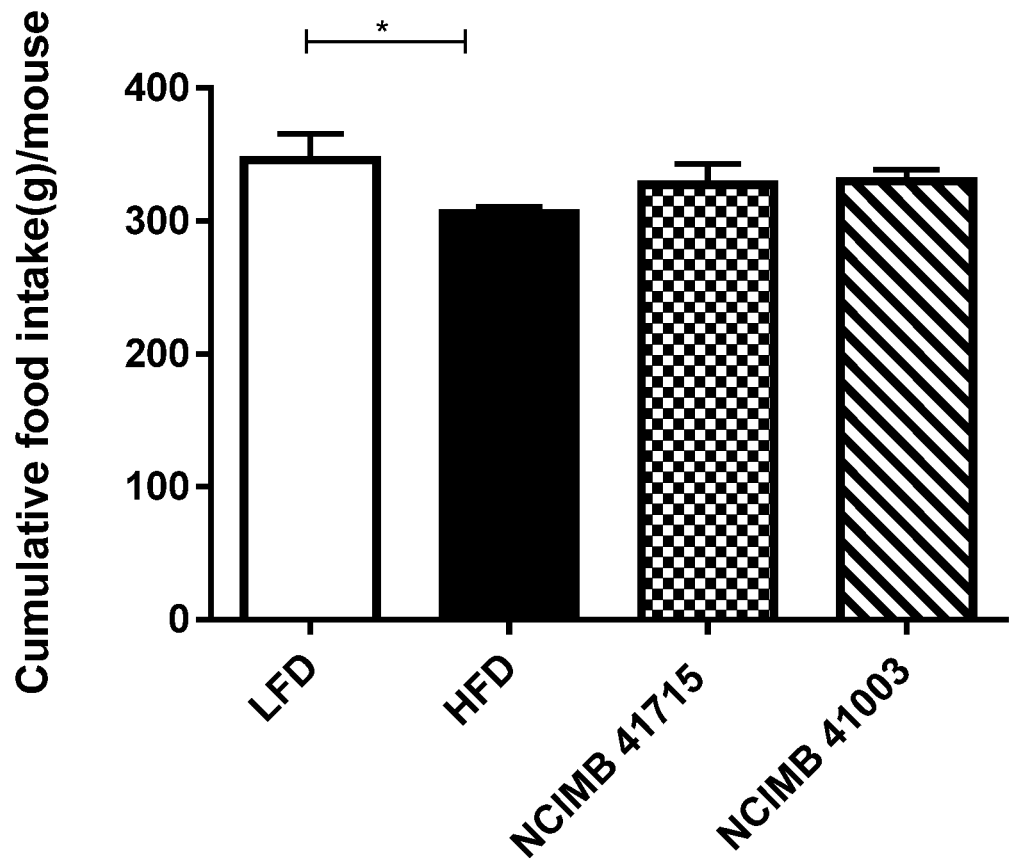
FIG. 14 shows the cumulative food intake per mouse following B. longum NCIMB 41715 and B. longum NCIMB 41003 administration relative to the high-fat diet (HFD) control group in the DIO mouse model.

FIG. 14: Cumulative food intake per mouse following *B. longum* NCIMB 41715 and *B. longum* NCIMB 41003 administration relative to the high-fat diet (HFD) control group in the DIO mouse model.

Figure 15:
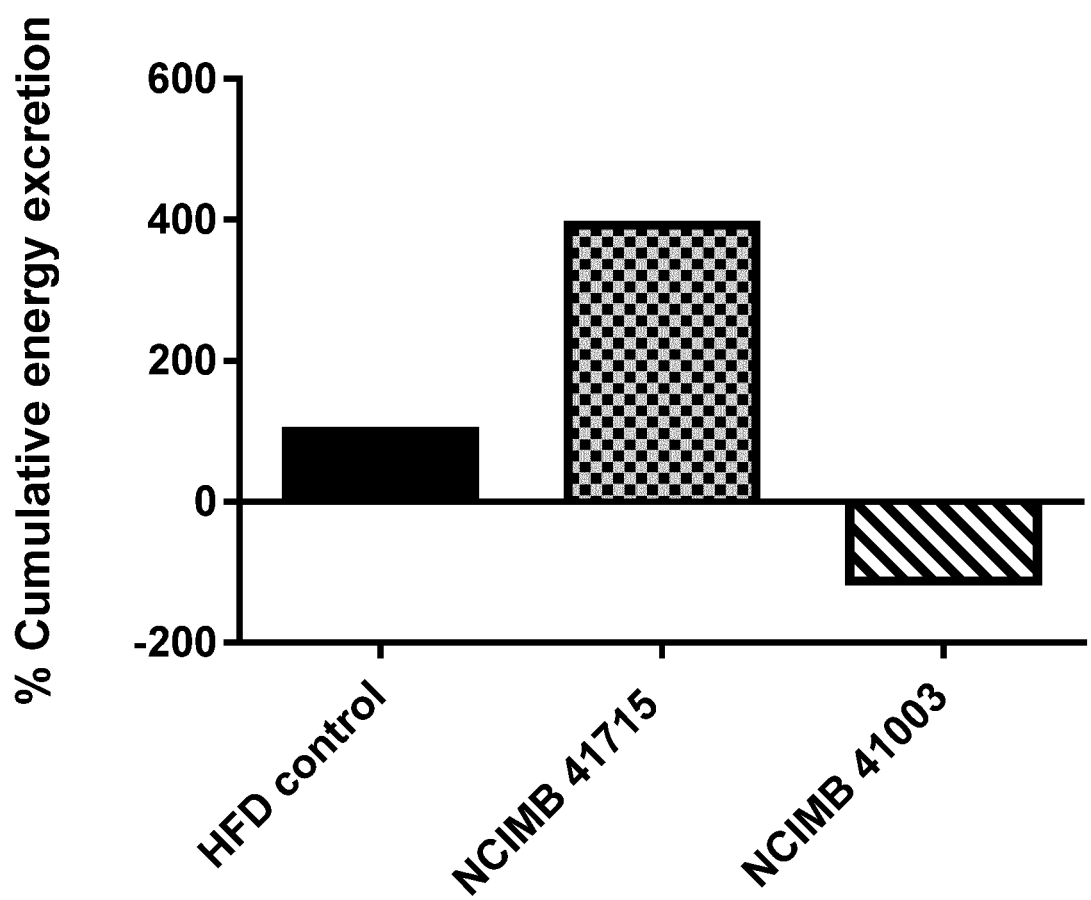
FIG. 15 presents the estimation of % cumulative energy excretion following B. longum NCIMB 41715 and B. longum NCIMB 41003 administration relative to the high-fat diet (HFD) control group in the DIO mouse model.

FIG. 15: Estimation of % cumulative energy excretion following *B. longum* NCIMB 41715 and *B. longum* NCIMB 41003 administration relative to the high-fat diet (HFD) control group in the DIO mouse model.

The low EPS producing *Lactobacillus* strain did not have any significant effect in this model.

Conclusion

*B. longum* NCIMB 41715 administration led to a significant reduction in fat mass by week sixteen for both strains. This was accompanied by a statistically significant reduction in subcutaneous fat and epididymal fat for *B. longum* NCIMB 41715. *B. longum* NCIMB 41715 administration led to a significant reduction in hepatic total cholesterol and triglyceride levels when compared to the HFD control group. Furthermore, a significant improvement on total cholesterol, LDL-cholesterol and VLDL-cholesterol was also observed with administration of *B. longum* NCIMB 41715 when compared to the HFD control group. Despite no significant difference in cumulative food intake over the course of the study, we observed an increase in % energy excretion for *B. longum* NCIMB 41715, suggesting that the administration of the hydrophobic *B. longum* NCIMB 41715 strain may reduce the amount of energy extracted from ingested food which could be responsible for the improvements in metabolic outcomes observed in this DIO mouse model.

Prebiotics

The introduction of probiotic organisms is accomplished by the ingestion of the micro-organism in a suitable carrier. It would be advantageous to provide a medium that would promote the growth of the strain in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit, and is termed synbiotic.

Other Active Ingredients

It will be appreciated that the strain may be administered prophylactically or as a method of treatment either on its own or with other probiotic and/or prebiotic materials as described above. In addition, the strain may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

Formulations

One or more of the strains of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition, a vaccine comprising one or more of the strains of the invention may be prepared using any suitable known method and may include a pharmaceutically acceptable carrier or adjuvant.

The strains of the invention may be formulated to facilitate controlled release such as a delayed release of the strain. For example, the formulation may be adapted to release the strain at a particular location in the gastrointestinal tract such as the small intestine or in the colon. To achieve such a controlled release the strain may be formulated in a capsule which has a coating which is adapted to release the strain at a particular location. A range of coatings are available to facilitate such controlled release. One such family of coatings are those available under the Trade Mark Eudragit.

All documents cited herein are, in relevant part, incorporated herein by reference.

The invention is not limited to the embodiments hereinbefore described, which may be varied in detail.

REFERENCES

ADAMS, E. L., RICE, P. J., GRAVES, B., ENSLEY, H. E., YU, H., BROWN, G. D., GORDON, S., MONTEIRO, M. A., PAPP-SZABO, E., LOWMAN, D. W., POWER, T. D., WEMPE, M. F. & WILLIAMS, D. L. 2008. Differential high-affinity interaction of dectin-1 with natural or synthetic glucans is dependent upon primary structure and is influenced by polymer chain length and side-chain branching. *J Pharmacol Exp Ther,* 325, 115-23.

ARONSSON, L., HUANG, Y., PARINI, P., KORACH-ANDRE, M., HAKANSSON, J., GUSTAFSSON, J. A., PETITERSSON, S., ARULAMPALAM, V. & RAFTER, J. 2010. Decreased fat storage by *Lactobacillus paracasei* is associated with increased levels of angiopoietin-like 4 protein (ANGPTL4). *PLoS One,* 5.

BACKHED, F., DING, H., WANG, T., HOOPER, L. V., KOH, G. Y., NAGY, A., SEMENKOVICH, C. F. & GORDON, J. I. 2004. The gut microbiota as an environmental factor that regulates fat storage. *Proc Natl Acad Sci USA,* 101, 15718-23.

BACKHED, F., MANCHESTER, J. K., SEMENKOVICH, C. F. & GORDON, J. I. 2007. Mechanisms underlying the resistance to diet-induced obesity in germ-free mice. *Proc Natl Acad Sci USA,* 104, 979-84.

BLAND, E. J., KESHAVARZ, T. & BUCKE, C. 2004. The influence of small oligosaccharides on the immune system. *Carbohydr Res,* 339, 1673-8.

CANI, P. D., AMAR, J., IGLESIAS, M. A., POGGI, M., KNAUF, C., BASTELICA, D., NEYRINCK, A. M., FAVA, F., TUOHY, K. M., CHABO, C., WAGET, A., DELMEE, E., COUSIN, B., SULPICE, T., CHAMONTIN, B., FERRIERES, J., TANTI, J. F., GIBSON, G. R., CASTEILLA, L., DELZENNE, N. M., ALESSI, M. C. & BURCELIN, R. 2007. Metabolic endotoxemia initiates obesity and insulin resistance. *Diabetes,* 56, 1761-72.

CANI, P. D., BIBILONI, R., KNAUF, C., WAGET, A., NEYRINCK, A. M., DELZENNE, N. M. & BURCELIN, R. 2008a. Changes in gut microbiota control metabolic endotoxemia-induced inflammation in high-fat diet-induced obesity and diabetes in mice. *Diabetes,* 57, 1470-81.

CANI, P. D., DELZENNE, N. M., AMAR, J. & BURCELIN, R. 2008b. Role of gut microflora in the development of obesity and insulin resistance following high-fat diet feeding. *Pathol Biol* (Paris), 56, 305-9.

FANNING, S., HALL, L. J., CRONIN, M., ZOMER, A., MACSHARRY, J., GOULDING, D., MOTHERWAY, M. O., SHANAHAN, F., NALLY, K., DOUGAN, G. & VAN SINDEREN, D. 2012. Bifidobacterial surface-exopolysaccharide facilitates commensal-host interaction through immune modulation and pathogen protection. *Proc Natl Acad Sci USA,* 109, 2108-13.

GREGOR, M. F. & HOTAMISLIGIL, G. S. 2011. Inflammatory mechanisms in obesity. *Annu Rev Immunol,* 29, 415-45.

GUH, D. P., ZHANG, W., BANSBACK, N., AMARSI, Z., BIRMINGHAM, C. L. & ANIS, A. H. 2009. The incidence of co-morbidities related to obesity and overweight: a systematic review and meta-analysis. *BMC Public Health,* 9, 88.

GUPTA, S., RICHARD, L. & FORSYTHE, A. 2015. The humanistic and economic burden associated with increasing body mass index in the EU5. *Diabetes Metab Syndr Obes,* 8, 327-38.

HIDALGO-CANTABRANA, C., LOPEZ, P., GUEIMONDE, M., DE LOS REYES-GAVILÁN, C., SUÁREZ, A., MARGOLLES, A. & RUAS-MADIEDO, P. 2012. Immune Modulation Capability of Exopolysaccharides Synthesised by Lactic Acid Bacteria and Bifidobacteria. *Probiotics and Antimicrobial Proteins*, 4, 227-237.

HIDALGO-CANTABRANA, C., NIKOLIC, M., LOPEZ, P., SUAREZ, A., MILJKOVIC, M., KOJIC, M., MARGOLLES, A., GOLIC, N. & RUAS-MADIEDO, P. 2014. Exopolysaccharide-producing *Bifidobacterium animalis* subsp. *lactis* strains and their polymers elicit different responses on immune cells from blood and gut associated lymphoid tissue. *Anaerobe*, 26, 24-30.

JONES, S. E., PAYNICH, M. L., KEARNS, D. B. & KNIGHT, K. L. 2014. Protection from intestinal inflammation by bacterial exopolysaccharides. *J Immunol*, 192, 4813-20.

KAHN, S. E., HULL, R. L. & UTZSCHNEIDER, K. M. 2006. Mechanisms linking obesity to insulin resistance and type 2 diabetes. *Nature*, 444, 840-6.

KANKAINEN, M., PAULIN, L., TYNKKYNEN, S., VON OSSOWSKI, I., REUNANEN, J., PARTANEN, P., SATOKARI, R., VESTERLUND, S., HENDRICKX, A. P., LEBEER, S., DE KEERSMAECKER, S. C., VANDERLEYDEN, J., HAMALAINEN, T., LAUKKANEN, S., SALOVUORI, N., RITARI, J., ALATALO, E., KORPELA, R., MATTILA-SANDHOLM, T., LASSIG, A., HATAKKA, K., KINNUNEN, K. T., KARJALAINEN, H., SAXELIN, M., LAAKSO, K., SURAKKA, A., PALVA, A., SALUSJARVI, T., AUVINEN, P. & DE VOS, W. M. 2009. Comparative genomic analysis of *Lactobacillus rhamnosus* GG reveals pili containing a human-mucus binding protein. *Proc Natl Acad Sci USA*, 106, 17193-8.

KOTZAMPASSI, K., GIAMARELLOS-BOURBOULIS, E. J. & STAVROU, G. 2014. Obesity as a consequence of gut bacteria and diet interactions. *ISRN Obes*, 2014, 651895.

LEE, H. Y., PARK, J. H., SEOK, S. H., BAEK, M. W., KIM, D. J., LEE, K. E., PAEK, K. S., LEE, Y. & PARK, J. H. 2006. Human originated bacteria, *Lactobacillus rhamnosus* PL60, produce conjugated linoleic acid and show anti-obesity effects in diet-induced obese mice. *Biochim Biophys Acta*, 1761, 736-44.

NAITO, E., YOSHIDA, Y., MAKINO, K., KOUNOSHI, Y., KUNIHIRO, S., TAKAHASHI, R., MATSUZAKI, T., MIYAZAKI, K. & ISHIKAWA, F. 2011. Beneficial effect of oral administration of *Lactobacillus casei* strain Shirota on insulin resistance in diet-induced obesity mice. *J Appl Microbiol*, 110, 650-7.

RIDAURA, V. K., FAITH, J. J., REY, F. E., CHENG, J., DUNCAN, A. E., KAU, A. L., GRIFFIN, N. W., LOMBARD, V., HENRISSAT, B., BAIN, J. R., MUEHLBAUER, M. J., ILKAYEVA, O., SEMENKOVICH, C. F., FUNAI, K., HAYASHI, D. K., LYLE, B. J., MARTINI, M. C., URSELL, L. K., CLEMENTE, J. C., VAN TREUREN, W., WALTERS, W. A., KNIGHT, R., NEWGARD, C. B., HEATH, A. C. & GORDON, J. I. 2013. Gut microbiota from twins discordant for obesity modulate metabolism in mice. *Science*, 341, 1241214.

TURNBAUGH, P. J., HAMADY, M., YATSUNENKO, T., CANTAREL, B. L., DUNCAN, A., LEY, R. E., SOGIN, M. L., JONES, W. J., ROE, B. A., AFFOURTIT, J. P., EGHOLM, M., HENRISSAT, B., HEATH, A. C., KNIGHT, R. & GORDON, J. I. 2009. A core gut microbiome in obese and lean twins. *Nature*, 457, 480-4.

TURNBAUGH, P. J., LEY, R. E., MAHOWALD, M. A., MAGRINI, V., MARDIS, E. R. & GORDON, J. I. 2006. An obesity-associated gut microbiome with increased capacity for energy harvest. *Nature*, 444, 1027-31.

VINDEROLA, G., PERDIGON, G., DUARTE, J., FARNWORTH, E. & MATAR, C. 2006. Effects of the oral administration of the exopolysaccharide produced by *Lactobacillus* kefiranofaciens on the gut mucosal immunity. *Cytokine*, 36, 254-60.

VOLMAN, J. J., RAMAKERS, J. D. & PLAT, J. 2008. Dietary modulation of immune function by beta-glucans. *Physiol Behav*, 94, 276-84.

VRIEZE, A., VAN NOOD, E., HOLLEMAN, F., SALOJARVI, J., KOOTTE, R. S., BARTELSMAN, J. F., DALLINGA-THIE, G. M., ACKERMANS, M. T., SERLIE, M. J., OOZEER, R., DERRIEN, M., DRUESNE, A., VAN HYLCKAMA VLIEG, J. E., BLOKS, V. W., GROEN, A. K., HEILIG, H. G., ZOETENDAL, E. G., STROES, E. S., DE VOS, W. M., HOEKSTRA, J. B. & NIEUWDORP, M. 2012. Transfer of intestinal microbiota from lean donors increases insulin sensitivity in individuals with metabolic syndrome. *Gastroenterology*, 143, 913-6.e7.

The invention claimed is:

1. A formulation for oral administration to a subject, the formulation comprising a strain of *Bifidobacterium longum* AH1362 deposited with the National Collection of Industrial, Food and Marine Bacteria (NCIMB) under accession number NCIMB 41715 and an ingestible carrier, wherein the formulation is in a form of a tablet or a powder.

2. The formulation as claimed in claim 1 which further comprises a probiotic material.

3. The formulation as claimed in claim 1 which further comprises a prebiotic material.

4. The formulation as claimed in claim 1 wherein the ingestible carrier comprises a food product.

5. The formulation as claimed in claim 1 which further comprises at least one of a protein or a peptide comprising glutamine/glutamate, a lipid, a carbohydrate, a vitamin, a mineral, a trace element, or a combination thereof.

6. The formulation as claimed in claim 1 wherein the strain is present in an amount of more than $10^6$ cfu per gram of the formulation.

7. The formulation as claimed in claim 1 which further comprises an adjuvant.

8. The formulation as claimed in claim 1 which further comprises a bacterial component.

9. The formulation as claimed in claim 1 which further comprises a drug entity.

10. The formulation as claimed in claim 1 which further comprises a biological compound.

11. The formulation as claimed in claim 1, wherein the strain of *Bifidobacterium longum* AH1362 is in the form of a powder.

12. The formulation as claimed in claim 11, wherein the formulation is in the form of a freeze-dried powder.

13. The formulation as claimed in claim 1 wherein the strain is in a form of viable cells or non-viable cells.

14. A foodstuff comprising the formulation of claim 1.

15. A medicament comprising the formulation of claim 1.

16. A capsule comprising the formulation of claim 1, wherein the formulation is in the form of a powder.

17. A method for preventing or treating a health condition, comprising administering a composition comprising a strain of *Bifidobacterium longum* AH1362 deposited with the National Collection of Industrial, Food and Marine Bacteria (NCIMB) under accession number NCIMB 41715 and ingestible carrier to a subject in need thereof, wherein the formulation is in a form of a tablet or a powder.

18. The method of claim 17, wherein the health condition includes one or more of obesity, obesity-related metabolic syndrome, or non-alcoholic fatty liver disease (NAFLD).

* * * * *